(12) United States Patent
Chen et al.

(10) Patent No.: US 7,867,999 B1
(45) Date of Patent: Jan. 11, 2011

(54) HYDROXYAMINO- AND AMINO-SUBSTITUTED PYRIDINE ANALOGS FOR TREATING RHO KINASE-MEDIATED DISEASES AND CONDITIONS

(75) Inventors: Hwang-Hsing Chen, Fort Worth, TX (US); Najam A. Sharif, Keller, TX (US); Mark R. Hellberg, Arlington, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 977 days.

(21) Appl. No.: 11/612,932

(22) Filed: Dec. 19, 2006

Related U.S. Application Data

(60) Provisional application No. 60/753,154, filed on Dec. 22, 2005.

(51) Int. Cl.
*A61K 31/35* (2006.01)
*A61K 31/44* (2006.01)
*A61K 31/551* (2006.01)
*C07D 213/75* (2006.01)

(52) U.S. Cl. .................. 514/217; 514/218; 514/252; 514/456; 514/913

(58) Field of Classification Search ................ 514/217, 514/218, 252, 456, 913
See application file for complete search history.

(56) References Cited

U.S. PATENT DOCUMENTS

| 5,798,380 | A  | 8/1998  | Kaufman et al. |
| 6,110,912 | A  | 8/2000  | Kaufman et al. |
| 6,218,410 | B1 | 4/2001  | Uehata et al. |
| 6,271,224 | B1 | 8/2001  | Kapin et al. |
| 6,403,590 | B1 | 6/2002  | Hellberg et al. |
| 6,451,825 | B1 | 9/2002  | Uehata et al. |
| 6,586,425 | B2 | 7/2003  | Kaufman et al. |
| 6,649,625 | B2 | 11/2003 | Azuma et al. |
| 6,673,812 | B1 | 1/2004  | Azuma et al. |
| 6,720,341 | B2 | 4/2004  | Moriyama et al. |
| 6,794,398 | B1 | 9/2004  | Nakamuta et al. |
| 2002/0045585 | A1 | 4/2002 | Kaufman et al. |

FOREIGN PATENT DOCUMENTS

| WO | WO 99/23113     |    | 5/1999  |
| WO | WO 01/68607     |    | 9/2001  |
| WO | WO 03/059913    |    | 7/2003  |
| WO | WO 03/062227    |    | 7/2003  |
| WO | WO 2004/000318  | A2 | 12/2003 |
| WO | WO 2004/009555  | A1 | 1/2004  |
| WO | WO 2004/024717  | A1 | 3/2004  |
| WO | WO 2004/084824  | A2 | 10/2004 |
| WO | WO 2004/085409  | A2 | 10/2004 |

OTHER PUBLICATIONS

Adachi et al., Studies on Pyrazines. I. The Syntheses of 2,3-Dihydroxypyrazines and Their Derivatices, J. Org. Chem., vol. 37(2):221-225, 1972.

Fukiage et al., Involvement of Phosphorylation of Myosin Phosphatase by ROCK in Trabecular Meshwork and Ciliary Muscle Contraction, Biochemical and Biophysical Research Communications, vol. 288:296-300, 2001.

Honjo et al., Effects of Rho-Associated Protein Kinase Inhibitor Y-27632 on Intraocular Pressure and Outflow Facility, Investigative Ophthalmology & Visual Science, vol. 42(1):137-144, 2001.

Honjo et al., Effects of Protein Kinase Inhibitor, HA1077, on Intraocular Pressure and Outflow Facility in Rabbit Eyes, Arch Ophthalmol., vol. 119:1171-1178, 2001.

Ishizaki et al., Pharmacological Properties of Y-27632, a Specific Inhibitor of Rho-Associated Kinases, Molecular Pharmacology, vol. 57:976-983, 2000.

Loge et al., Rho-kinase Inhibitors: Pharmacomodulations on the Lead Compound Y-32885, Journal of Enzyme Inhibition and Medicinal Chemistry, vol. 17(6):381-390, 2002.

Loge et al., Synethesis and Pharmacological Study of Rho-Kinase Inhibitors: Pharmacomodulations on the Lead Compound Fasudil, Journal of Enzyme Inhibition and Medicinal Chemistry, vol. 18(2):127-138, 2003.

Rao et al., Modulation of Aqueous Humor Outflow Facility by the Rho Kinase Specific Inhibitor Y-27632, Investigative Ophthalmology & Visual Science, vol. 42(5):1029-1037, 2001.

Sasaki et al., Novel and Specific Rho-Kinase Inhibitor, H-1152P, Directed Against the Rho-Kinase Involved Pathway, Cell Biol. Mol. Lett., vol. 6(2B):506, 2001.

Sasaki et al., The novel and specific Rho-kinase inhibitor (S)-(+)-2-methyl-1-[4-methyl-5-isoquinoline) sulfonyl]-homopiperazine as a probing molecule for Rho-kinase-involved pathway, Pharmacology & Therapeutics, vol. 93:225-232, 2002.

Sato et al., Studies on Pyrazines. Part 33. Synthesis of 2,3-Diaminopyrazines via [1,2,5]Thiadiazolo[3,4-b] pyrazines, J. Chem Research, (S):250-251, 1997.

Sato et al., Studies on Pyrazines; Part 30: Synthesis of Aminopyrazines for Azidopyrazines, Synthesis, vol. 9:931-934, 1994.

Sato et al., Studies on Pyrazines. Part 27. A New Deoxidative Nucleophilic Subsitution of Pyrazine N-Oxides; Synthesis of Azidopyrazines with Trimethylsilyl Azide, Journal Chem Society, vol. 7:885-888, 1994.

Sato et al., Studies on Pyrazines. 3. A Facile Synethic Method for 2,d-Diaminopyrazines, Journal Org. Chem., vol. 43(2):341-343, 1978.

Satoh et al., Pharmacological profile of hydroxy fasudil as a selective rho kinase inhibitor on ischemic brain damage, Life Sciences, vol. 69:1441-1443, 2001.

(Continued)

*Primary Examiner*—Ardin Marschel
*Assistant Examiner*—Zohreh Vakili
(74) *Attorney, Agent, or Firm*—Mark E. Flanigan

(57) ABSTRACT

Methods for using hydroxyamino- and amino-substituted pyridine analogs are disclosed herein to treat rho kinase-mediated diseases or rho kinase-mediated conditions, including controlling intraocular pressure and treating glaucoma, are disclosed. Ophthalmic pharmaceutical compositions useful in the treatment of eye diseases such as glaucoma, and additionally useful for controlling intraocular pressure, the compositions comprising an effective amount of hydroxyamino- and amino-substituted pyridine analogs, are disclosed herein.

16 Claims, No Drawings

OTHER PUBLICATIONS

Sharif et al., Pharmacological and Molecular Biological (RT-PCR) Characterization of Functional TP Prostanoid Receptors in Immortalized Human Non-Pigmented Ciliary Epithelial Cells, Journal of Ocular Pharmacology and Therapeutics, vol. 18(2):141-162, 2002.

Sharif et al., Pharmacology of [3H]Prostaglandin E1 [3H]Prostaglandin E2 and [3H]Prostaglandin F2a Binding to EP3 and FP Prostaglandin Receptor Binding . . . with Functional Data., Journal of Pharmacology and Experimental Therapeutics vol. 286:1094-1102 1998.

Sharif et al., Affinities, Selectivities, Potencies, and Intrinsic Activities of Natural and Synthetic Prostanoids Using Endogenous Receptors: Focus on DP Class Prostanoids, J of Pharmacology and Experimental Therapeutics, vol. 293(2):321-328 2000.

Sharif et al., Cloned human EP1 prostanoid receptor pharmacology characterized using radioligand binding techniques, vfol. 54:539-547, 2002.

Takami et al., Design and synthesis of Rho kinase inhibitors (I), Bioorganic & Medicinal Chemistry, vol. 12:2115-2137, 2004.

Thieme et al., Mediation of Calcium-Independent Contraction in Trabecular Meshwork through Protein Kinase C and Rho-A, Investigative Ophthalmology & Visual Science, vol. 41:4240-4246, 2000.

Tian et al., Effects of Topical H-7 on Outflow Facility, Intraocular Pressure, and Corneal Thickness in Monkeys, vol. 122:1171-1177, 2004.

Uehata et al., Calcium sensitization of smooth muscle mediated by a Rho-associated protein kinase in hypertension, Letters to Nature, vol. 389:990-994, 1997.

Waki et al., Reduction of intraocular pressure by topical administration of an inhibitor of the Rho-associated protein kinase, Current Eye Research, vol. 22(6):470-474, 2001.

Wettschureck et al., Rho/Rho-kinase mediated signaling in physiology and pathophysiology, Journal Molecular Medicine, vol. 80:629-638, 2002.

US 6,503,924, 01/2003, Azuma et al. (withdrawn)

HYDROXYAMINO- AND AMINO-SUBSTITUTED PYRIDINE ANALOGS FOR TREATING RHO KINASE-MEDIATED DISEASES AND CONDITIONS

This application claims priority under 35 U.S.C. §119 to U.S. Provisional to Patent Application No. 60/753,154, filed Dec. 22, 2005, the entire contents of which are incorporated herein by reference.

TECHNICAL FIELD OF THE INVENTION

The present invention is directed to hydroxyamino- and amino-substituted pyridine analogs, and the use of such compounds to treat rho kinase-mediated diseases and conditions. The invention is particularly directed to uses of such compounds for lowering and/or controlling normal or elevated intraocular pressure (IOP) and treating glaucoma.

BACKGROUND OF THE INVENTION

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated, but no apparent loss of visual function has occurred; such patients are considered to be at high risk for the eventual development of the visual loss associated with glaucoma. Some patients with glaucomatous field loss have relatively low intraocular pressure. These normotension or low tension glaucoma patients can also benefit from agents that lower and control IOP. If glaucoma or ocular hypertension is detected early and treated promptly with medications that effectively reduce elevated intraocular pressure, loss of visual function or its progressive deterioration can generally be ameliorated.

Drug therapies that have proven to be effective for the reduction of intraocular pressure include both agents that decrease aqueous humor production and agents that increase the outflow facility. Such therapies are in general administered by one of two possible routes, topically (direct application to the eye) or orally. However, pharmaceutical ocular anti-hypertension approaches have exhibited various undesirable side effects. For example, miotics such as pilocarpine can cause blurring of vision, headaches, and other negative visual side effects. Systemically administered carbonic anhydrase inhibitors can also cause nausea, dyspepsia, fatigue, and metabolic acidosis. Certain prostaglandins cause hyperemia, ocular itching, and darkening of eyelashes and periorbital tissue. Further, certain beta-blockers have increasingly become associated with serious pulmonary side-effects attributable to their effects on beta-2 receptors in pulmonary tissue. Sympathomimetics cause tachycardia, arrhythmia and hypertension. Such negative side-effects may lead to decreased patient compliance or to termination of therapy such that normal vision continues to deteriorate. Additionally, there are individuals who simply do not respond well when treated with certain existing glaucoma therapies. There is, therefore, a need for other therapeutic agents that control IOP.

The small rho GTPases are involved in many cellular functions including cell adhesion, cell motility, cell migration, and cell contraction. One of the main effectors of the cellular functions associated with this class of proteins is rho-associated coiled-coil-forming protein kinase (rho kinase) which appears to have an important role in the regulation of force and velocity of smooth muscle contraction, tumor cell metastasis and inhibition of neurite outgrowth. Rho kinase is a serine/threonine protein kinase that exists in two isoforms: ROCK1 (ROKβ) and ROCK2 (ROKα) [Wettschureck et al., *Journal of Molecular Medicine*, Vol. 80:629-638, 2002; Uehata et al., *Nature*, Vol. 389:990-994, 1997; Ishizaki et al., *Molecular Pharmacology*, Vol. 57:976-983, 2000; Loge et al., *Journal of Enzyme Inhibition and Medicinal Chemistry*, Vol. 17:381-390, 2002].

It has been found that certain inhibitors of rho kinase effectively lower and control normal and elevated IOP [Honjo, et al., *Investigative Opthalmology and Visual Science*, Vol. 42:137-144, 2001; Honjo et al., *Archives of Opthalmology*, Vol. 119:1171-1178, 2001; Rao et. al., *Investigative Opthalmology and Visual Science*, Vol. 42:1029-1690, 2001; Waki, *Current Eye Research*, Vol. 22:470-474, 2001; Tian et al., *Archives of Opthalmology*, Vol. 122:1171-1177, 2004]. Rho kinase inhibitors such as H-7 and Y-27632 inhibit ciliary muscle contraction and trabecular cell contraction, effects that may be related to the ocular hypotensive effect of this class of compounds [Thieme et al., *Investigative Opthalmology and Visual Science*, Vol. 41:4240-4246, 2001; Fukiage et al., *Biochemical and Biophysical Research Communications*, Vol. 288:296-300, 2001].

Compounds that act as rho kinase inhibitors are well known and have shown a variety of utilities. Pyridine, indazole, and isoquinoline compounds that have rho kinase activity are described by Takami et al., *Biorganic and Medicinal Chemistry*, Vol. 12:2115-2137, 2004. U.S. Pat. Nos. 6,218,410 and 6,451,825 disclose the use of rho kinase inhibitors for the treatment of hypertension, retinopathy, cerebrovascular contraction, asthma, inflammation, angina pectoris, peripheral circulation disorder, immature birth, osteoporosis, cancer, inflammation, immune disease, autoimmune disease and the like. U.S. Pat. No. 6,794,398 describes the use of a compound with rho kinase activity for the prevention or treatment of liver diseases. U.S. Pat. No. 6,720,341 describes the use of compounds with rho kinase activity for the treatment of kidney disease. WO 99/23113 describes the use of rho kinase inhibitors to block the inhibition of neurite outgrowth. WO 03/062227 describes 2,4-diaminopyrimidine derivatives as rho kinase inhibitors. WO 03/059913 describes bicyclic 4-aminopyrimidine analogs as rho kinase inhibitors. WO 02/100833 describes heterocyclic compounds as rho kinase inhibitors. WO 01/68607 describes amide derivatives as rho kinase inhibitors. WO 04/024717 describes amino isoquinoline derivatives as rho kinase inhibitors. WO 04/009555 describes 5-substituted isoquinoline derivatives as rho kinase inhibitors useful for treating glaucoma, bronchial asthma and chronic obstructive pulmonary disease. EP 1034793 describes the use of rho kinase inhibitors for the treatment of glaucoma.

U.S. Pat. Nos. 6,503,924; 6,649,625; and 6,673,812 disclose the use of amide derivatives that are rho kinase inhibitors for the treatment of glaucoma. U.S. Pat. Nos. 5,798,380 and 6,110,912 disclose a method for treating glaucoma using serine/threonine kinase inhibitors. U.S. Pat. No. 6,586,425 describes a method for treating glaucoma using serine/threonine kinase inhibitors. U.S. Patent Application Publication No. 2002/0045585 describes a method for treating glaucoma using serine/threonine kinase inhibitors.

The following references disclose the activity of isoquinoline sulfonamide analogs as rho kinase inhibitors: Y. Sasaki, *Cellular Biology Molecular Letters*, Vol. 6:506, 2001; Satoh et al., *Life Sciences*, Vol. 69:1441-1453, 2001; Sasaki, *Pharmacology and Therapeutics*, Vol. 93:225-232, 2002; Loge et al., *Journal of Enzyme Inhibition and Medicinal Chemistry*, Vol. 18:127-138. The use of certain isoquinolinesulfonyl compounds for the treatment of glaucoma has been disclosed in U.S. Pat. Nos. 6,271,224 and 6,403,590. Also, WO 04/000318 describes the use of amino-substituted monocycles as AKT-1 kinase modulators.

Several publications have described the synthesis of pyrazines. WO 04/084824 describes the preparation of biaryl substituted 6-membered heterocycles for use as sodium channel blockers. WO 04/085409 describes the preparation of libraries of compounds, including pyrazines, that are capable of binding to the active site of protein kinase. Other publications involving methods of pyrazine synthesis include: Sato et al., *Journal of Chemical Research*, Vol. 7:250-1, 1997; Sato et al., *Synthesis*, Vol. 9:931-4, 1994; Sato, *Journal of the Chemical Society*, Vol. 7:885-8, 1994; Sato, *Journal of Organic Chemistry*, Vol. 43(2):341-3, 1978; Adachi, et al., *Journal of Organic Chemistry*, Vol. 37(2):221-5, 1972.

SUMMARY OF THE INVENTION

The present invention is directed to hydroxyamino- and amino-substituted pyridines and derivatives described herein, and their use to treat rho kinase-mediated diseases and conditions.

The subject compounds of Formulas (I), (II), (III), and (IV) described below can be used to lower and/or control IOP associated with normal-tension glaucoma, ocular hypertension, and glaucoma in warm blooded animals, including man. In certain embodiments, when used to treat normal-tension glaucoma or ocular hypertension, the compounds may be formulated in pharmaceutically acceptable compositions suitable for topical delivery to the eye.

Another embodiment of the present invention contemplates an ophthalmic pharmaceutical composition useful in the treatment of glaucoma and control of intraocular pressure, comprising an effective amount of a compound according to Formulas (I), (II), (III), or (IV).

Another embodiment of the present invention comprises a method of controlling intraocular pressure comprising administering a therapeutically effective amount of an ophthalmic pharmaceutical composition useful in the treatment of glaucoma and control of intraocular pressure to a human or other mammal, where the composition comprises an effective amount of a compound according to Formulas (I), (II), (III), or (IV).

Yet other embodiments of the present invention comprise methods of treating rho kinase-mediated diseases or rho kinase-mediated conditions, which comprise administering to a human or other mammal a therapeutically effective amount of a compound or compounds according to Formulas (I), (II), (III), or (IV).

As used herein, the term "rho kinase-mediated disease" or "rho kinase-mediated condition," means any disease or other deleterious condition in which rho kinase is known to play a role. Such conditions include, without limitation, hypertension, glaucoma, retinopathy, cerebrovascular contraction, ocular hypertension, normal-tension glaucoma, chronic obstructive pulmonary disease, asthma, inflammation, angina pectoris, peripheral circulation disorder, immature birth, osteoporosis, cancer, inflammation, immune disease, autoimmune disease.

The foregoing brief summary broadly describes the features and technical advantages of certain embodiments of the present invention. Additional features and technical advantages will be described in the detailed description of the invention that follows. Novel features which are believed to be characteristic of the invention will be better understood from the detailed description of the invention when considered in connection with any accompanying examples. However, examples provided herein are intended to help illustrate the invention or assist with developing an understanding of the invention, and are not intended to be definitions of the invention's scope.

DETAILED DESCRIPTION OF THE INVENTION

In one embodiment, the present invention provides a compound of Formula (I):

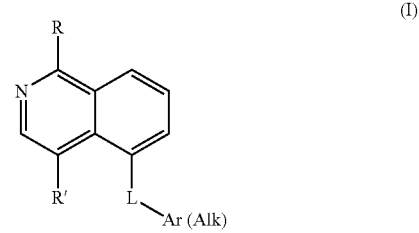

(I)

wherein
R=H, R', $NH_2$, NHOH, NHCOR', NHOR', or NR'OH;
R'=alkyl or aryl;
L=CO, CR'R', SO, or $SO_2$; and
Ar (Alk)=an aromatic aryl, heteroaryl, or alkyl group substituted with one or more amines.

In another embodiment of the present invention, a compound of Formula (II) is provided:

(II)

wherein
R=H, R', $NH_2$, NHOH, NHCOR', NHOR', or NR'OH;
R'=alkyl or aryl;
Y=N, CH or CMe; and
Ar (Alk)=an aromatic aryl, heteroaryl, or alkyl group substituted with one or more amines.

In still another embodiment of the present invention, a compound of Formula (III) is provided:

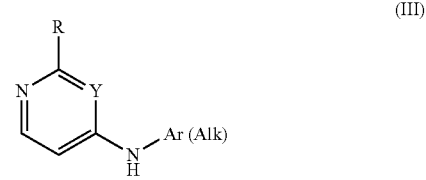

(III)

wherein
R=H, R', $NH_2$, NHOH, NHCOR', NHOR', or NR'OH;
R'=alkyl or aryl;
Y=N, CH or CMe; and
Ar (Alk)=an aromatic aryl, heteroaryl, or alkyl group substituted with one or more amines.

In another embodiment, the present invention provides a compound of Formula (IV):

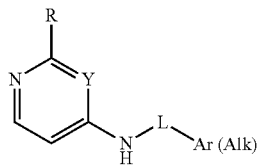

wherein:
R=H, R', NH$_2$, NHOH, NHCOR', NHOR', or NR'OH;
R'=alkyl or aryl;
Y=N, CH or CMe;
L=CO, CR'R', SO, or SO$_2$; and
Ar (Alk)=an aromatic aryl, heteroaryl, or alkyl group substituted with one or more amines.

It is recognized that compounds of Formulas (I)-(IV) can contain one or more chiral centers. This invention contemplates all enantiomers, diastereomers, and mixtures of Formulas (I)-(IV) thereof.

Furthermore, certain embodiments of the present invention comprise pharmaceutically acceptable salts of compounds according to Formula (I)-(IV). Pharmaceutically acceptable salts comprise, but are not limited to, soluble or dispersable forms of compounds according to Formulas (I)-(IV) that are suitable for treatment of disease without undue undesirable effects such as allergic reactions or toxicity. Representative pharmaceutically acceptable salts include, but are not limited to, acid addition salts such as acetate, citrate, benzoate, lactate, or phosphate and basic addition salts such as lithium, sodium, potassium, or aluminum.

The term "aryl" as used herein refers to a monocyclic, bicyclic or tricyclic ring system having a total of five to fourteen ring members, wherein at least one ring in the system is aromatic and wherein each ring in the system contains 3 to 7 ring members. The term "aryl" may be used interchangeably with the term "aryl ring".

The term "heterocycle", "heterocyclyl", or "heterocyclic" as used herein means non-aromatic, monocyclic, bicyclic or tricyclic ring systems having three to fourteen ring members in which one or more ring members is a heteroatom, wherein each ring in the system contains 3 to 7 ring members.

The term "heteroaryl" refers to monocyclic, bicyclic or tricyclic ring systems having three to fourteen ring members wherein at least one ring in the system is aromatic, at least one ring in the system contains one or more heteroatoms, and wherein each ring in the system contains 3 to 7 ring members.

In the above definitions, the total number of carbon atoms in a substituent group is indicated by the C$_{i-j}$ prefix, where the numbers i and j define the number of carbon atoms; this definition includes straight chain, branched chain, and cyclic alkyl or (cyclic alkyl)alkyl groups.

It is important to recognize that a substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

In the above compounds represented by Formulas (I)-(IV), the addition of hydroxyamino and amino substitutents in certain embodiments increases hydrogen bonding to rho kinase hydrogen-bond acceptors. Additionally, certain hydroxyamino pyridine analogs have improved solubility characteristics and may increase drug bioavailability and activity.

The following compounds are particularly preferred in certain embodiments of the present invention:

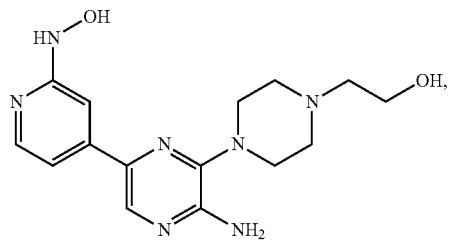

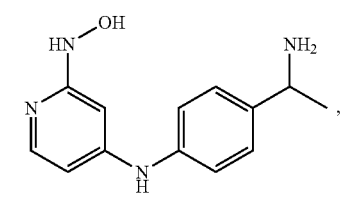

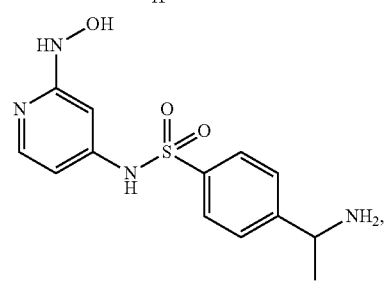

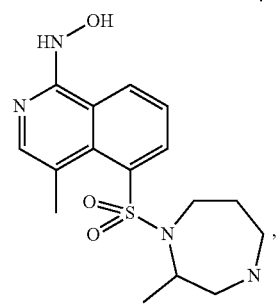

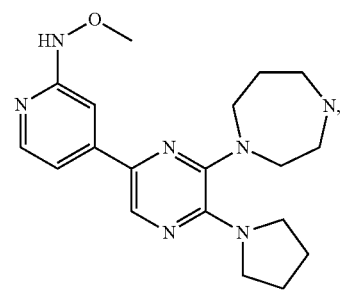

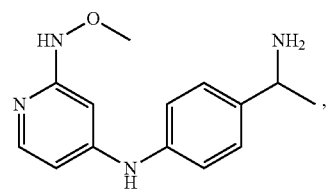

-continued

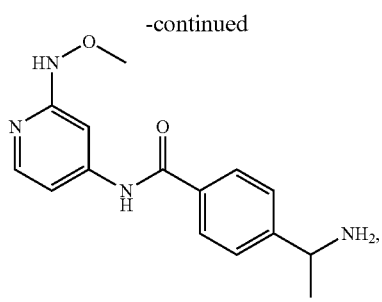

The following compounds are also preferred: N-[5-([1,4-Diazepane-1-sulfonyl)-isoquinolin-1-yl]-hydroxylamine; N-[5-([1,4-Diazepane-1-sulfonyl)-isoquinolin-1-yl]-O-methyl-hydroxylamine; 4-(1-Amino-ethyl)-cyclohexanecarboxylic acid (2-hydroxyamino-pyridin-4-yl)-amide; 4-(1-Amino-ethyl)-cyclohexanecarboxylic acid (2-methoxyamino-pyridin-4-yl)-amide; 4-(1-Amino-ethyl)-N-(2-hydroxyamino-pyridin-4-yl)-benzamide; 4-(1-Amino-ethyl)-N-(2-methoxyamino-pyridin-4-yl)-benzamide; N-[4-(6-[1,4]Diazepan-1-yl-5-pyrrolidin-1-yl-pyrazin-2-yl)-pyridin-2-yl]-hydroxylamine; N-[4-(6-[1,4]Diazepan-1-yl-5-pyrrolidin-1-yl-pyrazin-2-yl)-pyridin-2-yl]-O-methyl-hydroxylamine; N-[4-(6-[1,4]Diazepan-1-yl-5-pyrrolidin-1-yl-pyrazin-2-yl)-pyridin-2-yl]-hydroxylamine; and N-[4-(6-[1,4]Diazepan-1-yl-5-pyrrolidin-1-yl-pyrazin-2-yl)-pyridin-2-yl]-O-methyl-hydroxylamine.

SYNTHESIS EXAMPLES

The compounds of Formulas (I)-(IV) can be synthesized using the general and specific examples set forth below.

The compounds of Formula (I) can be prepared by using one of several synthetic procedures. For example, N-[5-(1,4]diazepane-1-sulfonyl)-isoquinolin-1-yl]-hydroxylamine can be prepared from the corresponding isoquinoline or 1-bromoisoquinoline as outlined in Scheme 1 below. As used herein, "Pg" denotes a suitable protective group to assure that a particular atom is not modified during the indicated chemical reaction.

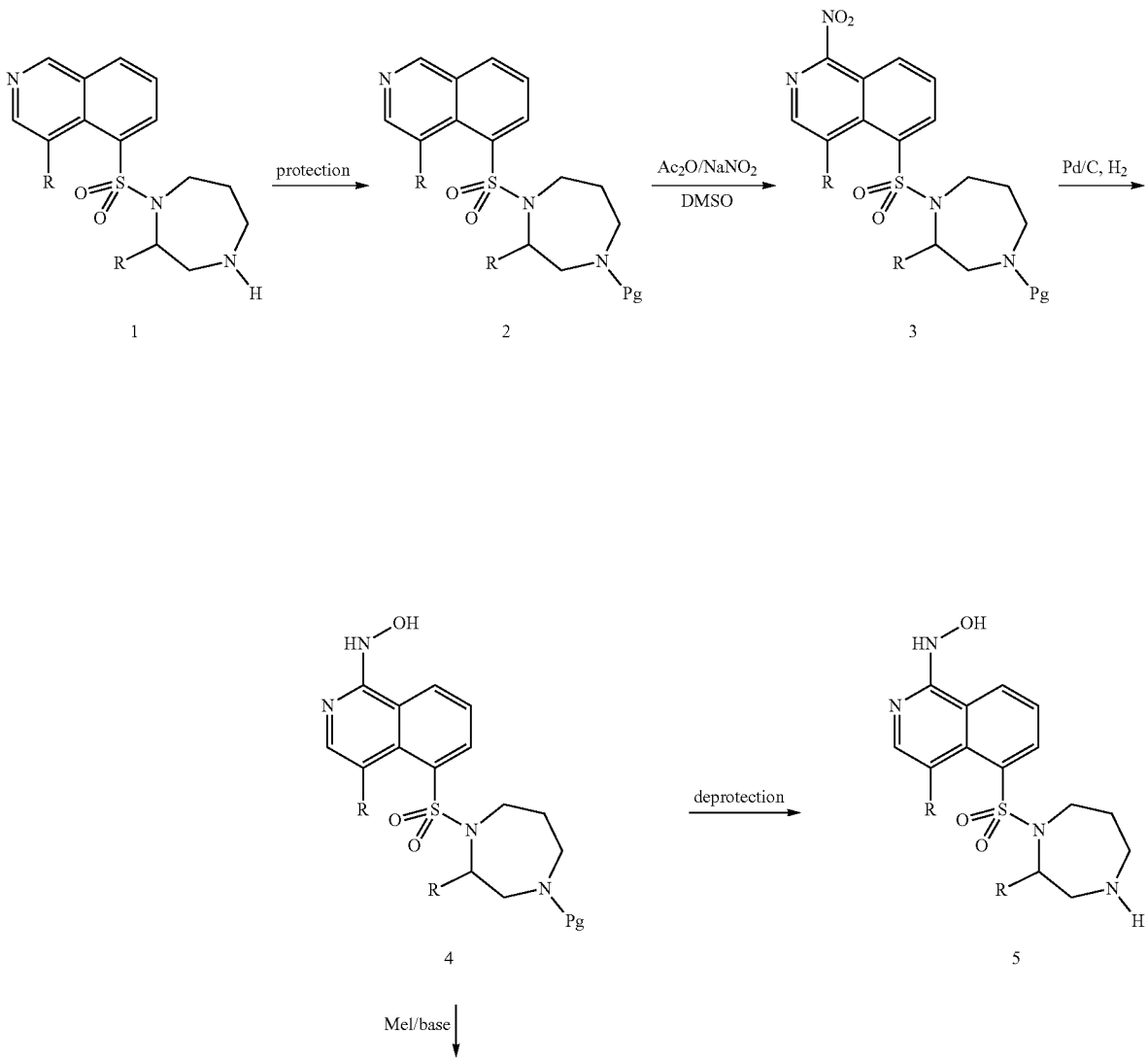

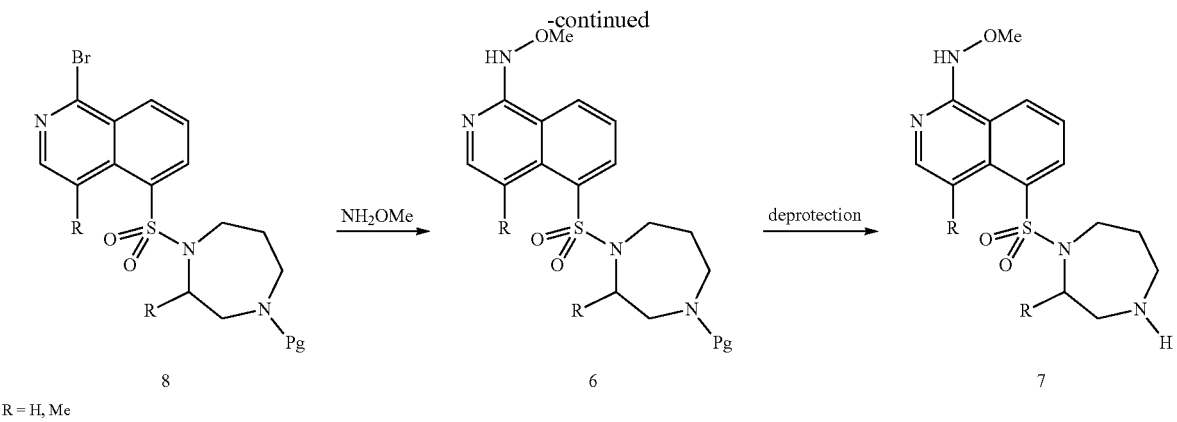
R = H, Me
The compounds of Formulas (II), (III), and (IV) with pyridine template can be prepared by using one of several synthetic procedures. For example, 4-(1-amino-ethyl)-N-(2-hydroxyamino-pyridin-4-yl)-benzamide can be prepared from the corresponding pyridine or 1-bromopyridine as shown in Scheme 2 below.
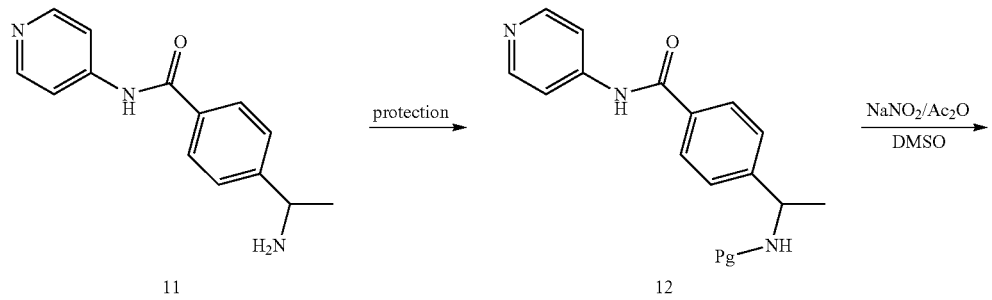
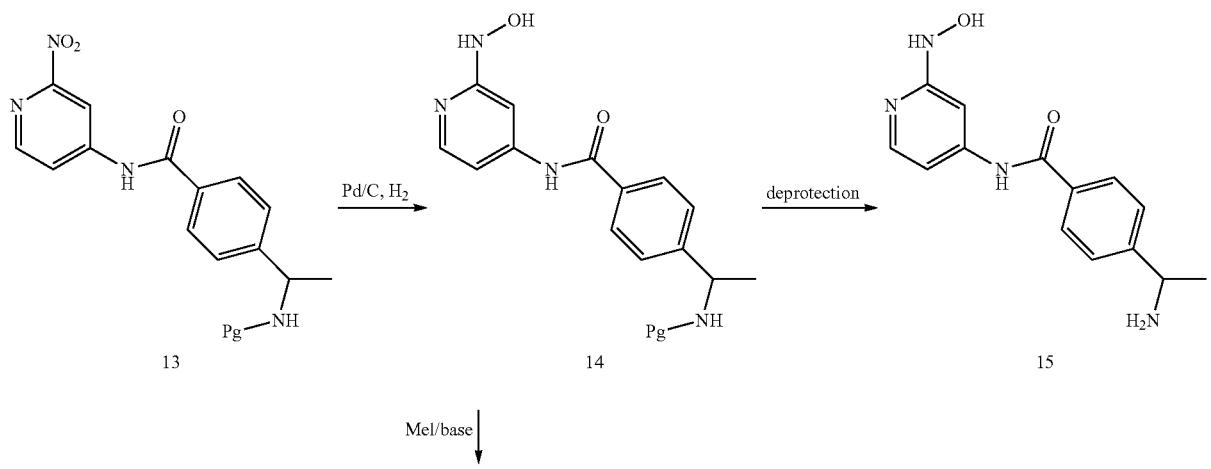

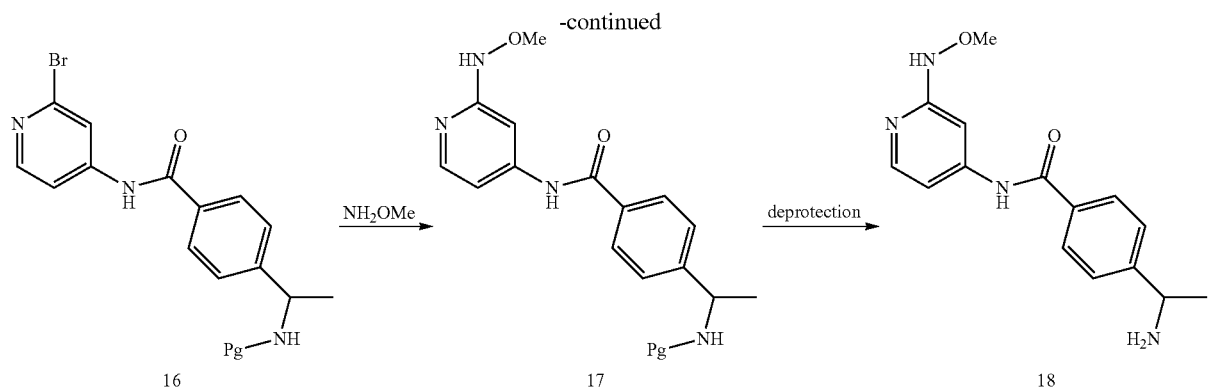
-continued 16     17     18

Using the procedures described in Schemes 1 and 2 shown above, the examples shown below, and well known procedures, one skilled in the art can prepare the compounds disclosed herein. In addition, Example 1 below provides a specific protocol for synthesis of a compound according to an embodiment of the present invention.

Modes of Delivery

The compounds of Formula (I)-(IV) can be incorporated into various types of ophthalmic formulations for delivery. Formula (I)-(IV) compounds may be delivered directly to the eye (for example: topical ocular drops or ointments; slow release devices such as pharmaceutical drug delivery sponges implanted in the cul-de-sac or implanted adjacent to the sclera or within the eye; periocular, conjunctival, sub-tenons, intracameral, intravitreal, or intracanalicular injections) or systemically (for example: orally, intravenous, subcutaneous or intramuscular injections; parenterally, dermal or nasal delivery) using techniques well known by those of ordinary skill in the art. It is further contemplated that the agents of the invention may be formulated in intraocular insert or implant devices.

The compounds of Formulas (I)-(IV) are preferably incorporated into topical ophthalmic formulations with a pH of about 4-8 for delivery to the eye. The compounds may be combined with opthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an opthalmologically acceptable surfactant to assist in dissolving the compound. Furthermore, the ophthalmic solution may contain an agent to increase viscosity such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle such as mineral oil, liquid lanolin, or white petrolatum. Sterile ophthalmic gel formulations may be prepared by suspending the compound in a hydrophilic base prepared from the combination of, for example, carbopol-974, or the like, according to the published formulations for analogous ophthalmic preparations; preservatives and tonicity agents can be incorporated.

Compounds in preferred embodiments are contained in a composition in amounts sufficient to lower TOP in patients experiencing elevated IOP and/or maintaining normal IOP levels in glaucoma patients. Such amounts are referred to herein as "an amount effective to control IOP," or more simply "an effective amount." The compounds will normally be contained in these formulations in an amount 0.01 to 5 percent by weight/volume ("w/v %"), but preferably in an amount of 0.25 to 2 w/v %. Thus, for topical presentation 1 to 2 drops of these formulations would be delivered to the surface of the eye 1 to 4 times per day, according to the discretion of a skilled clinician.

The compounds of Formulas (I)-(IV) can also be used in combination with other glaucoma treatment agents, such as, but not limited to, n-blockers, prostaglandin analogs, carbonic anhydrase inhibitors, $\alpha_2$ agonists, miotics, and neuroprotectants.

Determination of Biological Activity

The ability of certain compounds of Formulas (I)-(IV) to inhibit rho kinase is evaluated by means of in vitro assays. Human recombinant Rho kinase (ROKa/ROCK-II, (aa 11-552), human active, catalog #14-451, Upstate Biotechnology Co., Lake Placid, N.Y.), $MgCl_2$/ATP cocktail, and enzyme substrate (Upstate) is used.

Fluorescence polarization assays are performed using a Biomek 2000 Robotic Workstation (Beckman Instruments, Palo Alto, Calif.) in a 96-well plate format. The assays are performed utilizing the IMAP ROCK II kit (Molecular Devices, Sunnyvale, Calif.) as follows. Substrate and ATP concentrations used are 200 nM and 10 µM, respectively, while the enzyme concentration is $3.96 \times 10^{-3}$ units per well. The substrate, enzyme, and ATP dilutions are made with the reaction buffer provided by the vendor. Test compounds are diluted in 10:10 DMSO-ethanol (vol/vol). For the actual assays, the various components are added into black, clear bottom, 96-well plates (Costar, Corning, N.Y.) in a final volume of 20 µl per well. After the enzyme reaction (60 min at 23° C.), 60 µl of the binding solution (IMAP kit, provided by vendor) is added per well and incubated for an additional 30 minutes in the dark at 23° C. Fluorescence polarization of the reaction mixtures is then measured on the Analyst™ HT instrument (Molecular Devices, Sunnyvale, Calif.).

The data generated are then analyzed using a non-linear, iterative, sigmoidal-fit computer program purchased from IDBS (Emeryville, Calif.) and as previously described (Sharif et al., *J. Pharmacol. Exp. Ther.*, Vol. 286:1094-1102, 1998; Sharif et al., *J. Pharmacol. Expt. Ther.*, Vol. 293:321-328, 2000; Sharif et al., *J. Ocular Pharmacol. Ther.*, Vol.

18:141-162, 2002a; Sharif et al., *J. Pharmac. Pharmacol.*, Vol. 54:539-547, 2002b) to generate the inhibition constants for the test compounds.

The following compounds according to Formula (I) were analyzed using the protocol above to determine their IC$_{50}$ constants.

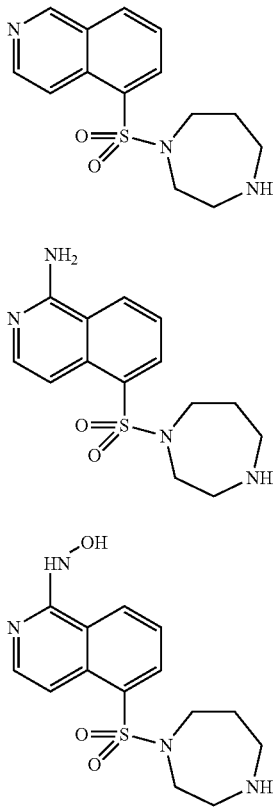

Table 1 presents the results of the analysis of the above compounds, indicating that these compounds are biologically active and inhibit rho kinase activity.

TABLE 1

| Rho kinase II Binding Data | |
| --- | --- |
| Example | IC$_{50}$, uM |
| 1 | 1.21 |
| 2 | 2.11 |
| 3 | 39.0 |

EXAMPLES

The following examples are provided to illustrate certain embodiments of the invention, but should not be construed as implying any limitations to the claims. For example, the phrase "Compound of Formula (I)" in Example 2 means that the formulation described in the respective Example is believed to be suitable for any compound according to Formula (I), (II), (III), or (IV).

Example 1

Preparation of N-[5-([1,4-Diazepane-1-sulfonyl)-isoquinolin-1-yl]-hydroxylamine hydrochloride Step A: 4-(Isoquinoline-5-sulfonyl)-[1,4]diazepane-1-carboxylic acid tert-butyl ester To a stirred suspension of isoquinoline-5-sulfonylchloride hydrochloride (3.00 g, 11.4 mmol) in anhydrous methylene chloride (100 mL) was added tert-butyl 1-homopiperazine carboxylate (3.00 g, 15.0 mmol) and triethylamine (4.36 g, 43.1 mmol). The mixture was stirred for 3 h, evaporated to dryness, mixed with a saturated solution of sodium bicarbonate (100 mL) and extracted with ethyl acetate (80 mL×2). The combined extracts were dried, filtered and evaporated to give an oil (4.45 g, 100%). LCMS (+APCI) m/z 392 (M+H).

Step B: 4-(1-Nitro-isoquinoline-5-sulfonyl)-[1,4]diazepane-1-carboxylic acid tert-butyl ester To a stirred solution of the isoquinoline from step A (1.17 g, 3.0 mmol) in anhydrous DMSO (12 mL) was added sodium nitrite (1.24 g, 18 mmol). To the mixture was added slowly over 30 min a solution of acetic anhydride (1.84 g, 18 mmol) in anhydrous DMSO (12 mL). The mixture was stirred overnight and TLC showed most starting material remained. More sodium nitrite (1.24 g, 18 mmol) and acetic anhydride (1.84 g, 18 mmol) in anhydrous DMSO (12 mL) was added and stirring was continued for about 1 h. During this period yellow solid precipitated and TLC showed a new product at Rf 0.5 (hexane/EtOAc 1:1). The mixture was poured into a saturated aqueous solution of sodium bicarbonate (100 mL) and extracted with EtOAc (100 mL×2). Chromatography on silica eluting with 20% EtOAc/Hexane gave an oil. (0.81 g, 62%). LCMS (+APCI) m/z 454 (M+H+NH3).

Step C: 4-(1-Hydroxyamino-isoquinoline-5-sulfonyl)-[1,4]diazepane-1-carboxylic acid tert-butyl ester A solution of the nitro-isoquinoline from step B (0.81 mmol, 1.86 mmol) and Pd/C (10%, 0.081 g) in methanol (50 mL) was stirred under hydrogen overnight, filtered and evaporated to give a crude oil. Chromatography on silica eluting with a gradient of 20% to 70% of EtOAc/Hexane gave an oil. (0.43 g, 55%). LCMS (+APCI) m/z 423 (M+H).

Step D: N-[5-([1,4-Diazepane-1-sulfonyl)-isoquinolin-1-yl]-hydroxylamine hydrochloride To the hydroxylamine from step C (0.19 g, 0.45 mmol) was added trifluoroacetic acid (2 mL) and stirred overnight. The volatiles were evaporated and the reside was dissolved in methanol and treated with 2 N HCl/EtOH (1 mL) The mixture was dried to give a yellowish solid that was washed with ethyl acetate and dried in vacuum at 78° C. overnight to afford a solid (0.13 g, 81%). LCMS (+APCI) m/z 322 (M+H).

| EXAMPLE 2 | |
| --- | --- |
| Ingredients | Concentration (w/v %) |
| Compound of Formula (I) | 0.01-2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |

-continued

EXAMPLE 2

| Ingredients | Concentration (w/v %) |
| --- | --- |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 3

| Ingredients | Concentration (w/v %) |
| --- | --- |
| Compound of Formula (II) | 0.01-2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 4

| Ingredients | Concentration (w/v %) |
| --- | --- |
| Compound of Formula (III) | 0.01-2% |
| Guar gum | 0.4-6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

EXAMPLE 5

| Ingredients | Concentration (w/v %) |
| --- | --- |
| Compound of Formula (IV) | 0.01-2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

What is claimed is:

1. An ophthalmic pharmaceutical composition useful in the treatment of glaucoma and control of intraocular pressure, comprising an effective amount of a compound according to Formula (I), Formula (II), Formula (III), or Formula (IV), or a pharmaceutically acceptable salt thereof:

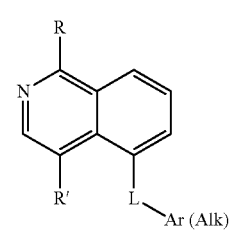

(I)

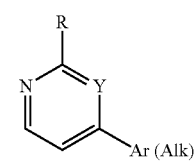

(II)

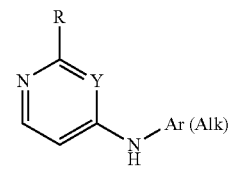

(III)

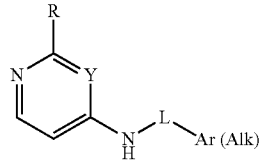

(IV)

wherein
R=H, R', NH$_2$, NHOH, NHCOR', NHOR', or NR'OH;
R'=alkyl or aryl;
Y=N, CH or CMe;
L=CO, CR'R', SO, or SO$_2$; and
Ar (Alk)=an aromatic aryl, heteroaryl, or alkyl group substituted with one or more amines; and
a pharmaceutically acceptable vehicle therefore.

2. The composition of claim 1, further comprising a compound selected from the group consisting of:
opthalmologically acceptable preservatives, surfactants, viscosity enhancers, penetration enhancers, gelling agents, hydrophobic bases, vehicles, buffers, sodium chloride, and water.

3. The composition of claim 1, wherein said composition comprises from about 0.01 percent weight/volume to about 5 percent weight/volume of said compound.

4. The composition of claim 1, wherein said composition comprises from about 0.25 percent weight/volume to about 2 percent weight/volume of said compound.

5. A method of controlling intraocular pressure comprising:
applying a therapeutically effective amount of an ophthalmic pharmaceutical composition useful in the treatment of glaucoma and control of intraocular pressure to the affected eye of a human or other mammal, the composition comprising an effective amount of a compound according to Formula (I), Formula (II), Formula (III), or Formula (IV):

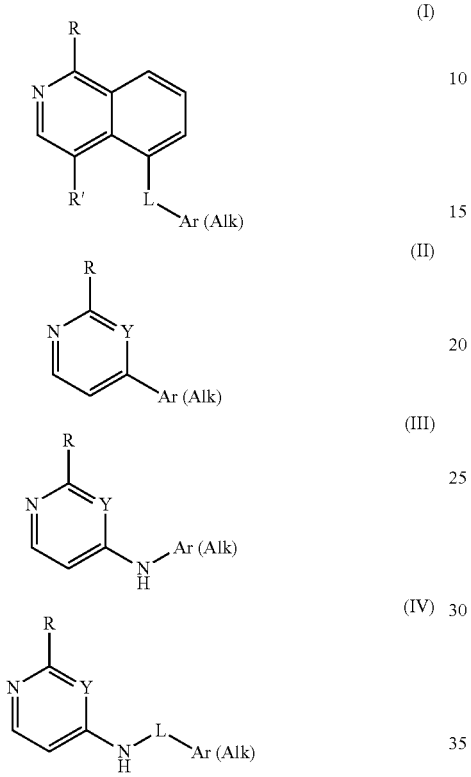

wherein
R=H, R', NH₂, NHOH, NHCOR', NHOR', or NR'OH;
R'=alkyl or aryl;
Y=N, CH or CMe;
L=CO, CR'R', SO, or SO₂; and
Ar (Alk)=an aromatic aryl, heteroaryl, or alkyl group substituted with one or more amines; and
a pharmaceutically acceptable vehicle thereof.

6. The method of claim 5, wherein said applying comprises applying 1 to 2 drops of a composition comprising from about 0.01 percent weight/volume to about 5 percent weight/volume of a compound according to Formula (I), Formula (II), Formula (III), or Formula (IV) 1 to 4 times daily.

7. The method of claim 5, wherein said composition further comprises a glaucoma treatment agent in addition to a compound of Formula (I), (II), (III), or (IV).

8. The method of claim 7 wherein at least one glaucoma treatment agent is selected from the group consisting of:
β-blockers, prostaglandin analog, carbonic anhydrase inhibitors, α₂ agonists, miotics, neuroprotectants, and combinations thereof.

9. A method of treating rho kinase-mediated diseases or rho kinase-mediated conditions, which comprises administering to a human or other mammal a therapeutically effective amount of a compound according to Formula (I), Formula (II), Formula (III), or Formula (IV):

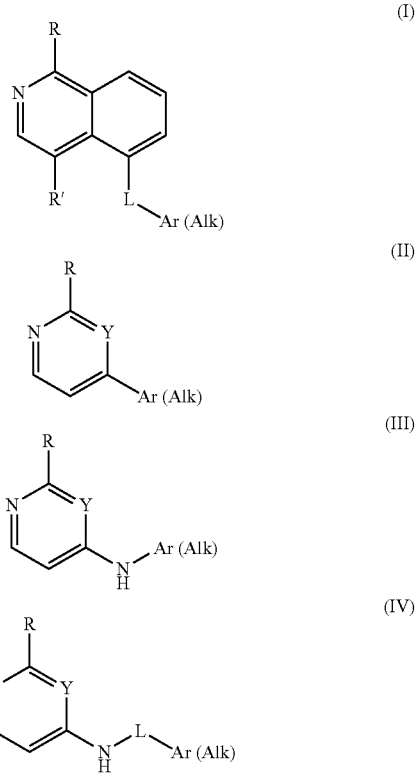

wherein
R=H, R', NH₂, NHOH, NHCOR', NHOR', or NR'OH;
R'=alkyl or aryl;
Y=N, CH or CMe;
L=CO, CR'R', SO, or SO₂; and
Ar (Alk)=an aromatic aryl, heteroaryl, or alkyl group substituted with one or more amines; and
a pharmaceutically acceptable vehicle therefore.

10. The method of claim 9 wherein said administering comprises applying 1 to 2 drops of a composition comprising from about 0.01 percent weight/volume to about 5 percent weight/volume of compound according to Formula (I), Formula (II), Formula (III), or Formula (IV), 1 to 4 times daily.

11. The method of claim 9 wherein said composition further comprises a glaucoma treatment agent in addition to a compound of Formula (I), (II), (III), or (IV).

12. The method of claim 11 wherein the glaucoma treatment agent is selected from the group consisting of:
β-blockers, prostaglandin analogs, carbonic anhydrase inhibitors, α₂ agonists, miotics, neuroprotectants, and combinations thereof.

13. A compound represented by Formula (I), or a pharmaceutically acceptable salt thereof:

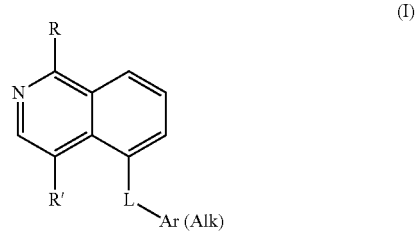

wherein

R=H, R', NH₂, NHOH, NHCOR', NHOR', or NR'OH;
R'=alkyl or aryl;
L=CO, CR'R', SO, or SO₂; and
Ar (Alk)=an aromatic aryl, heteroaryl, or alkyl group substituted with one or more amines.

14. A compound represented by Formula (II), or a pharmaceutically acceptable salt thereof:

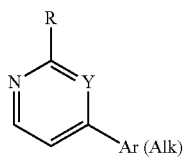

(II)

wherein

R=H, R', NH₂, NHOH, NHCOR', NHOR', or NR'OH;
R'=alkyl or aryl;
Y=N, CH or CMe; and
Ar (Alk)=an aromatic aryl, heteroaryl, or alkyl group substituted with one or more amines.

15. A compound represented by Formula (III), or a pharmaceutically acceptable salt thereof:

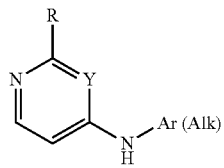

(III)

wherein

R=H, R', NHOH, NHCOR', NHOR', or NR'OH;
R'=alkyl or aryl;
Y=N, CH or CMe;
L=CO, CR'R', SO, or SO₂; and
Ar (Alk)=an aromatic aryl, heteroaryl, or alkyl group substituted with one or more amines.

16. A compound represented by Formula (IV), or a pharmaceutically acceptable salt thereof:

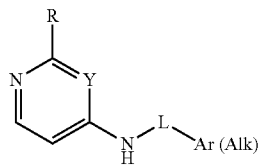

(IV)

wherein

R=H, R', NH₂, NHOH, NHCOR', NHOR', or NR'OH;
R'=alkyl or aryl;
Y=N, CH or CMe;
L=CO, CR'R', SO, or SO₂; and
Ar (Alk)=an aromatic aryl, heteroaryl, or alkyl group substituted with one or more amines.

* * * * *